(12) United States Patent
Pingleton et al.

(10) Patent No.: US 9,108,017 B2
(45) Date of Patent: Aug. 18, 2015

(54) METHOD OF MAKING TUBING HAVE DRAINAGE HOLES

(75) Inventors: Edward D. Pingleton, Rancho Santa Margarita, CA (US); Ghassan Sakakine, Rancho Santa Margarita, CA (US); Boun Pravong, Rancho Santa Margarita, CA (US); Michael Palermo, Rancho Santa Margarita, CA (US); Nathalie Raad, Rancho Santa Margarita, CA (US)

(73) Assignee: Applied Medical Resources Corporation, Rancho Santa Magarita, CA (US)

( * ) Notice: Subject to any disclaimer, the term of this patent is extended or adjusted under 35 U.S.C. 154(b) by 56 days.

(21) Appl. No.: 13/427,031

(22) Filed: Mar. 22, 2012

(65) Prior Publication Data

US 2012/0241076 A1    Sep. 27, 2012

Related U.S. Application Data

(60) Provisional application No. 61/466,348, filed on Mar. 22, 2011.

(51) Int. Cl.
*B32B 38/04* (2006.01)
*A61M 25/00* (2006.01)
(Continued)

(52) U.S. Cl.
CPC ............ *A61M 25/0012* (2013.01); *B29C 53/60* (2013.01); *B29C 2793/0045* (2013.01); *B29L 2031/753* (2013.01)

(58) Field of Classification Search
CPC ...................... A61M 25/0012; A61M 25/0013; A61M 25/0015; A61M 25/005; B29C 2793/0018; B29C 2793/0054

USPC ............ 604/526, 527; 156/64, 379, 252, 253, 156/378, 526, 527, 250, 353, 143
See application file for complete search history.

(56) References Cited

U.S. PATENT DOCUMENTS 3,585,707 A    6/1971    Stevens
3,618,613 A    11/1971    Schulte
(Continued)

FOREIGN PATENT DOCUMENTS

EP    0 810 033    12/1997

OTHER PUBLICATIONS

European Patent Office, International Searching Authority, Search Report and Written Opinion of International Application No. PCT/US2012/029964, entitled "Method of Making Tubing Having Drainage Holes", mailed Jun. 27, 2012.
(Continued)

*Primary Examiner* — Jacob T Minskey
*Assistant Examiner* — Vishal I Patel
(74) *Attorney, Agent, or Firm* — Rimas Lukas (57) ABSTRACT

A method for manufacturing a kink-resistant tube having drainage holes is provided. A wire is coated with plastic material and wound around a mandrel forming a plurality of windings. The wound coated wire is heated until the plastic coating material melts and bonds the wire windings to form a wire-reinforced sheath having wire-containing sections and non-wire containing sections. Alternatively, a coated or non-coated wire is wound around a mandrel together with separate polymer filament material and then heated. A filament having an elongated cross-section may be employed with the major axis of the elongated cross-section substantially parallel to the longitudinal axis of the sheath. At least one non-wire containing section is identified by passing light through at least one wall of the wire-reinforced sheath. Image capture and analysis via an optical system and microprocessor automatically identify regions to target a drill for forming holes in the non-wire containing sections.

14 Claims, 6 Drawing Sheets

(51) Int. Cl.
  *B29C 53/60* (2006.01)
  *B29L 31/00* (2006.01)

(56) References Cited

U.S. PATENT DOCUMENTS

| | | |
|---|---|---|
| 4,172,473 A | 10/1979 | Lefere |
| 4,531,933 A | 7/1985 | Norton |
| 4,634,432 A | 1/1987 | Kocak |
| 4,690,175 A | 9/1987 | Ouchi |
| 4,705,511 A | 11/1987 | Kocak |
| 4,728,328 A | 3/1988 | Hughes |
| 4,747,849 A | 5/1988 | Galtier |
| 4,913,683 A | 4/1990 | Gregory |
| 4,931,037 A | 6/1990 | Wetterman |
| 5,059,375 A | 10/1991 | Lindsay |
| 5,061,257 A | 10/1991 | Martinez |
| 5,069,673 A | 12/1991 | Shwab |
| 5,163,431 A | 11/1992 | Griep |
| 5,180,376 A | 1/1993 | Fischell |
| 5,201,723 A | 4/1993 | Quinn |
| 5,246,445 A | 9/1993 | Yachia |
| 5,454,795 A | 10/1995 | Samson |
| 5,472,435 A | 12/1995 | Sutton |
| 5,558,737 A | 9/1996 | Brown |
| 5,569,197 A | 10/1996 | Helmus |
| 5,658,264 A | 8/1997 | Samson |
| 5,702,373 A | 12/1997 | Samson |
| 5,762,637 A | 6/1998 | Berg |
| 5,782,811 A * | 7/1998 | Samson et al. ................ 604/527 |
| 5,795,341 A | 8/1998 | Samson |
| 5,853,400 A | 12/1998 | Samson |
| 5,863,366 A | 1/1999 | Snow |
| 5,891,090 A | 4/1999 | Thornton |
| 5,891,112 A | 4/1999 | Samson |
| 5,902,290 A | 5/1999 | Peacock |
| 5,928,279 A | 7/1999 | Shannon |
| 5,951,539 A | 9/1999 | Nita |
| 6,059,770 A | 5/2000 | Peacock |
| 6,117,106 A | 9/2000 | Wasicek |
| 6,130,406 A | 10/2000 | Cheer |
| 6,143,013 A | 11/2000 | Samson |
| 6,159,187 A | 12/2000 | Park |
| 6,197,014 B1 | 3/2001 | Samson |
| 6,332,892 B1 | 12/2001 | Desmond, III |
| 6,451,005 B1 | 9/2002 | Saitou |
| 6,494,908 B1 | 12/2002 | Huxel |
| 6,524,268 B2 | 2/2003 | Hayner |
| 6,569,150 B2 | 5/2003 | Teague |
| 6,582,472 B2 | 6/2003 | Hart |
| 6,589,227 B2 | 7/2003 | Sønderskov Klint |
| 6,709,465 B2 | 3/2004 | Mitchell |
| 6,719,804 B2 | 4/2004 | St. Pierre |
| 6,764,519 B2 | 7/2004 | Whitmore, III |
| 6,790,223 B2 | 9/2004 | Reever |
| 6,790,225 B1 | 9/2004 | Shannon |
| 6,824,553 B1 | 11/2004 | Samson |
| 6,887,215 B2 | 5/2005 | McWeeney |
| 6,981,964 B2 | 1/2006 | Rioux |
| 7,004,965 B2 | 2/2006 | Gross |
| 7,112,226 B2 | 9/2006 | Gellman |
| 7,141,038 B2 | 11/2006 | Whalen |
| 7,163,562 B2 | 1/2007 | Datta |
| 7,166,134 B2 | 1/2007 | Datta |
| 7,169,139 B2 | 1/2007 | Teague |
| 7,169,187 B2 | 1/2007 | Datta |
| 7,291,180 B2 | 11/2007 | St. Pierre |
| 7,316,663 B2 | 1/2008 | Whitmore, III |
| 7,387,641 B2 | 6/2008 | Schmitt |
| 7,445,684 B2 | 11/2008 | Pursley |
| 7,550,012 B2 | 6/2009 | Lavelle |
| 7,691,078 B2 | 4/2010 | Rioux |
| 2002/0177904 A1 | 11/2002 | Huxel |
| 2003/0040803 A1 | 2/2003 | Rioux |
| 2004/0087886 A1 | 5/2004 | Gellman |
| 2004/0097881 A1 * | 5/2004 | Brustad et al. ........... 604/164.07 |
| 2004/0267349 A1 | 12/2004 | Richter |
| 2005/0027160 A1 | 2/2005 | Siegel |
| 2005/0165366 A1 | 7/2005 | Brustad |
| 2005/0187510 A1 | 8/2005 | McWeeney |
| 2005/0240278 A1 | 10/2005 | Aliski |
| 2007/0050006 A1 | 3/2007 | Lavelle |
| 2007/0215268 A1 | 9/2007 | Pingleton |
| 2007/0276466 A1 | 11/2007 | Lavelle |
| 2008/0086215 A1 | 4/2008 | St. Pierre |
| 2008/0091275 A1 | 4/2008 | Ducharme |
| 2008/0097275 A1 | 4/2008 | Whitmore |
| 2008/0183299 A1 | 7/2008 | Monga |
| 2008/0199506 A1 | 8/2008 | Horres |
| 2008/0208083 A1 | 8/2008 | Lin |
| 2009/0030363 A1 | 1/2009 | Gellman |
| 2009/0192592 A1 | 7/2009 | Asgari |
| 2009/0192627 A1 | 7/2009 | Shin |
| 2009/0204055 A1 | 8/2009 | Lennox |
| 2010/0072659 A1 | 3/2010 | Gellman |
| 2010/0076574 A1 | 3/2010 | Gellman |
| 2010/0145467 A1 | 6/2010 | Davoudi |
| 2010/0152862 A1 | 6/2010 | Rioux |
| 2011/0030876 A1 * | 2/2011 | Larson ........................ 156/64 |

OTHER PUBLICATIONS

International Bureau of WIPO, International Preliminary Report on Patentability for International Application No. PCT/US2012/029964, titled Method of Making Medical Tubing Having Drainage Holes, dated Sep. 24, 2013.

* cited by examiner

METHOD OF MAKING TUBING HAVE DRAINAGE HOLES

CROSS-REFERENCE TO RELATED APPLICATIONS

This application claims priority to U.S. Provisional Application No. 61/466,348 filed on Mar. 22, 2011 entitled "Method of making medical tubing having drainage holes" which is hereby incorporated by reference in its entirety.

FIELD

This invention generally relates to novel methods for manufacturing medical devices, more specifically, thin-walled, kink-resistant medical tubing having drainage holes and adapted for insertion into a body tissue or cavities.

BACKGROUND

Medical tubing includes tubing used as stents, catheters, drain tubes, access ports, endoscope bodies and the like. The requirements for each type of medical tubing will depend on its use. For example, a medical tubing may need to be very flexible and yet pushable, or it may need to be thin-walled and yet, kink-resistant. Often, the tubing may require holes for drainage. The tubing may need to exhibit these properties in only specific regions.

Various methods have been described for manufacturing medical tubing. Most medical tubing is extruded from a single plastic material in a continuous forming process. While certain characteristics or variations may be imparted to the extruded tubing by altering the speed or the tension of the extruded material as it exits and cools from the extrusion machine, the variations are limited by the fact that a single material is extruded. Recent advances in extrusion technology have allowed the co-extrusion of multiple materials. This provides some usable variations in extruded tubing. Nevertheless, this is still a linear process and is still limited by the continuous flow of the extruded materials. Moreover, extrusion methods do not yield medical tubing having both very thin walls and high kink-resistance. However, it is relatively easy to add drainage holes to extruded tubing, for example, by drilling or puncturing where desired.

Recently, an alternative method for producing medical tubing has been described. For example, in U.S. Pat. No. 7,005,026, a method is described wherein a wire, coated with a plastic material, is wrapped around a mandrel forming a plurality of windings. The wound coated wire is then heated until the plastic material melts and bonds the windings to form a wire-reinforced sheath. See also U.S. Pat. No. 7,534,317, describing a method of manufacturing medical tubing by coating a mandrel with a first layer of plastic material to form an inner tube, placing a braid over the inner tube, placing a spring reinforcement over the braid, and then coating the braid with a second layer of plastic material to form an outer tube of a braid-reinforced sheath.

Medical tubing produced by these methods can be both thin walled and kink resistant, but it may be difficult to incorporate drainage holes, as care must be taken not to sever the wire/braid/spring reinforcement incorporated into the tubing. As the skilled practitioner will appreciate, a break in the wire reinforcement, whether the wire is formed from metal, plastic, or some other material, may reduce the column and/or hoop strength of the reinforced tube, and produce potentially hazardous broken ends. It may also produce undesirable debris or even projections or scars disrupting the outer surface of the tubing.

Accordingly, there is a need for medical tubing that is both thin walled and kink resistant and that includes drainage holes. There is further a need for a method of incorporating drainage holes into wire-reinforced tubing that avoids cutting or nicking the wire.

SUMMARY

According to one aspect of the invention, a method for manufacturing a kink-resistant tube having drainage holes is provided. The method includes the step of coating a wire with a plastic material. The coated wire is wound around a mandrel forming a plurality of windings. The wound coated wire is heated until the plastic material of the wire melts and bonds the windings forming a wire-reinforced sheath having wire-containing sections and non-wire containing sections. At least one non-wire containing section is identified and at least one hole is formed in the non-wire containing section.

According to another aspect of the invention, a method for manufacturing a kink-resistant tube having drainage holes is provided. The method includes the step of coating a wire with a plastic material. The coated wire is wound around a mandrel forming a plurality of windings. The wound coated wire is heated until the plastic material of the wire melts and bonds the windings forming a wire-reinforced sheath having wire-containing sections and non-wire containing sections. At least two wire containing sections are identified and at least one hole is formed between the two wire-containing sections.

According to another aspect of the invention, a method for manufacturing a kink-resistant tube having drainage holes is provided. The method includes the step of winding a wire together with a plastic filament around a mandrel forming a plurality of alternating windings of wire and plastic filament. The wound wire and the filament are heated until the polymer material of the wire and the filament melt and bond the windings forming a wire-reinforced sheath having wire-containing sections and non-wire-containing sections. At least one non-wire containing section is identified or detected and at least one hole is formed in the non-wire containing section.

DETAILED DESCRIPTION

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing, for example, the structures and/or methodologies that are described in the publications which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

U.S. Pat. No. 7,005,026 describes a process for manufacturing medical tubing having thin walls and high kink resistance. This process is shown in FIGS. 1A-1D and summarized below.

Figure 1A:
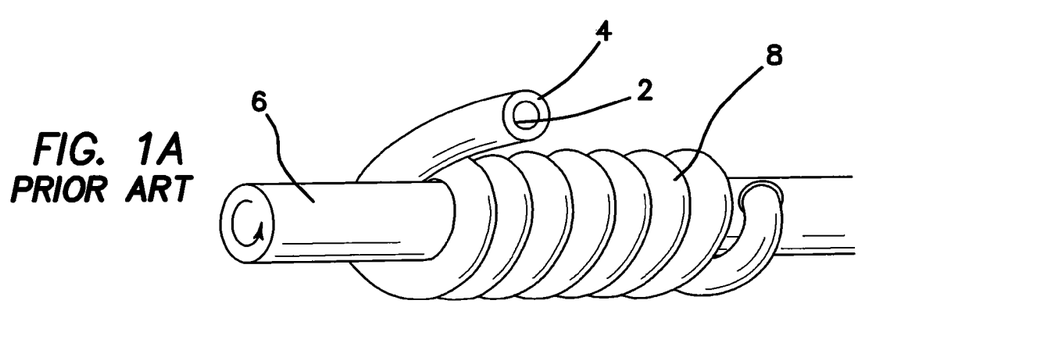
FIGS. 1A-1D show steps in a prior art process for manufacturing a thin walled, kink resistant tube.
Figure 1B:
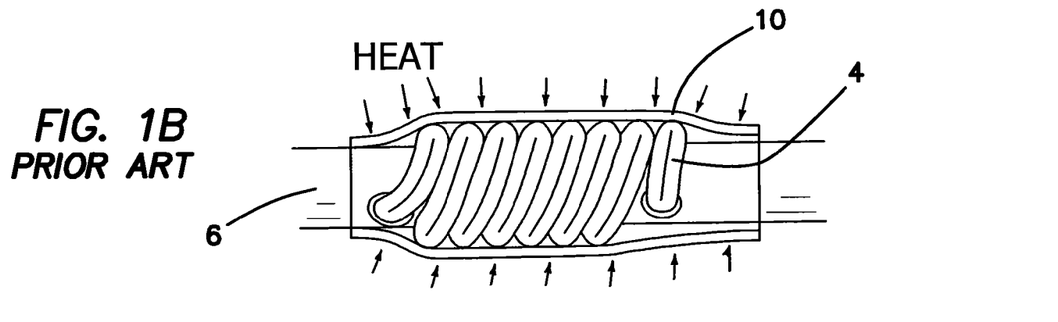
Figure 1C:
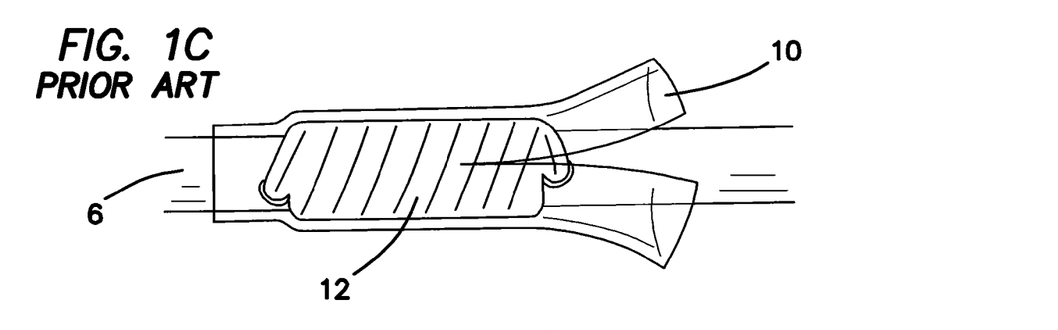
Figure 1D:
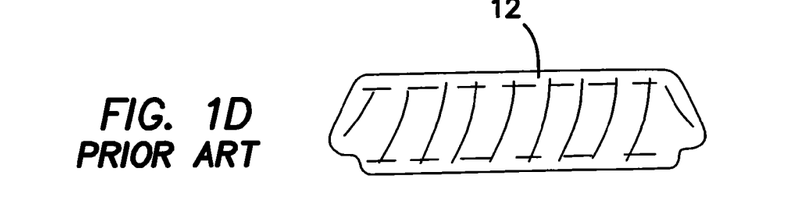

With initial reference to FIG. 1A, a wire 2 is coated with a plastic material 4, for example, in a coextrusion process. The coated wire is then wrapped or wound on a straight or tapered mandrel 6 forming a desired profile of the resultant tube such as a reinforcement coil or spring 8 as illustrated in FIG. 1A. After wrapping, the wound coated wire is heated as shown in FIG. 1B until the plastic material 4 melts and bonds the windings. FIG. 1B shows a shrink tube 10 being used to help compress the windings. The plastic material 4 melts and bonds the windings to form the resultant tube or sheath 12 and the shrink tube 10 is removed as shown in FIG. 1C. Once cooled, the sheath 12 is removed from the mandrel 6 leaving the wire reinforced tube 12 as shown in FIG. 1D. It should be noted that the wound coated wire is heated until the plastic material 4 is formed above, below and in between the wire windings. The wire/plastic coextrusion may be round, have straight edges that can be laid adjacent to each other when winding or have interlocking shapes. The wound coated wire may be heated in one of several ways including: (i) capturing the windings within a shrink tube 10 as illustrated in FIG. 1B and heating until the shrink tube 10 encapsulates all the windings and the sheath is formed; and (ii) using a mold to compress the windings and heating the windings until the sheath is formed. The heat shrink tube 10 or mold is then cut or removed from the sheath 12 as illustrated in FIG. 1C. That is, after the plastic material such as polyurethane has melted together to form the sheath 12 with spring reinforcement, the shrink tube 10 is cut away and the mandrel 6 is removed. The resulting wire-reinforced tube 12 can then be further modified by tip forming, ink measurement marking, hydrophilic coating, pigtail coil forming and the like.

As will be appreciated, this de-molting manufacturing process involves three steps: 1) wire coating; 2) de-molting in which the coated wire is wound around the mandrel and heated to form a tube; and 3) top level assembly, where tips, markings, pigtail coils, etc. are added to the de-molted tube. The present invention is directed to modifications of this de-molting method that make the process more efficient and cost-effective, and/or that incorporate a hole-drilling process into the top level assembly step. More generally, the present invention is directed to a method of detecting appropriate drill sites for incorporating holes during manufacture of medical tubing having a wire reinforcement, regardless of the method used to manufacture the tube.

Figure 2A:
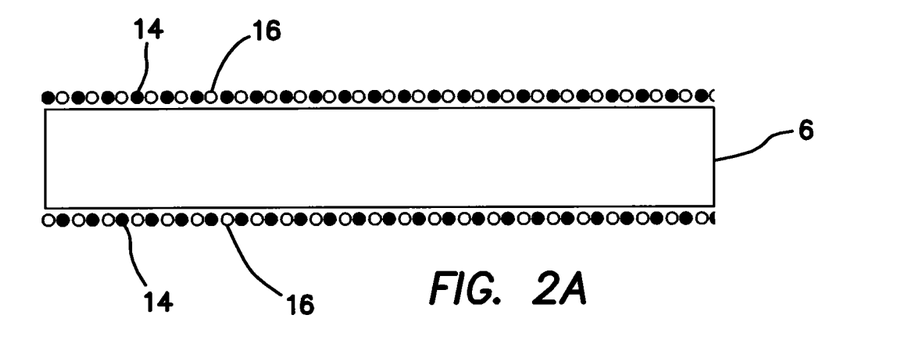
FIGS. 2A-2B show a method for manufacturing a thin walled, kink resistant tube by alternately winding an uncoated wire and a polymeric filament around a mandrel.
Figure 2B:
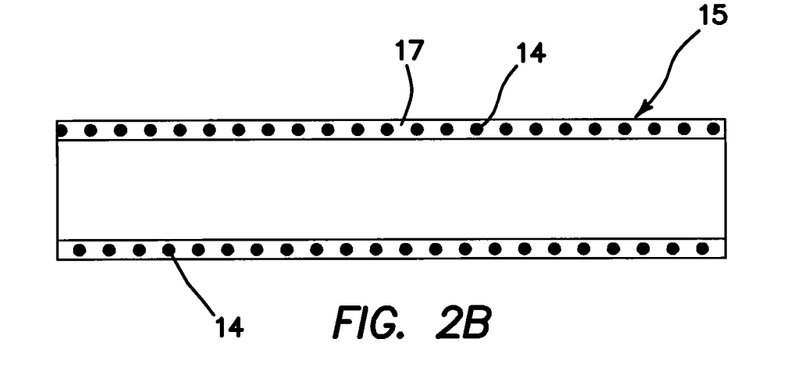

A first embodiment of the present invention is directed to a modification of the de-molting process that does not require the use of an extruder to coat the wire, thereby, obviating step one of the manufacturing process. In this embodiment, shown in FIG. 2A, a raw metal wire 14 is alternatively wound with a filament 16 comprising a polymeric material around the mandrel 6. It is appreciated that the polymeric material can be polyurethane, a thermoplastic, a thermoset, a silicon thermoset polymer or any plastic or polymeric material having hard and/or soft durometer. This is then heated as described above with respect to the prior art, causing the polymeric material to melt over and around the raw metal wire, forming a wire reinforced tube containing the wire 14 and polymer material 17 as shown in FIG. 2B. Tubing made according to this process will be thin walled, flexible and kink resistant. In addition, the time and costs associated with the manufacturing process are reduced by eliminating the initial step of coextruding wire with polymeric material to coat the wire before winding it on the mandrel 6.

A second embodiment of the present invention incorporates a hole-creating step in the top-level assembly and will be described below.

A wire, preferably stainless steel, titanium, tantalum, tantalum with a stainless steel core, or other radiopaque, MRI-safe material, is coated with a polymer and wound around a mandrel. Suitable polymeric materials include hard plastics, glass-filled polymers, KEVLAR® fiber, fishing wire or other hard fibers. The wire and mandrel are inserted into a silicone tube to form a de-molting assembly. The de-molting assembly is placed into a heated oven and heated until the polymer melts and forms on the inner diameter to the mandrel and the outer diameter to the silicone tube. The assembly is removed from the oven and cooled. The mandrel is removed from the silicone tube. The resulting fused tube is removed from the mandrel. A light is directed at the resulting tube to identify light and dark sections on the tube and holes are drilled at desired intervals, drilling only through the relatively light sections of the tube where the wire is not present relative to the darker wire-containing sections. Optionally, a tip is added to the tube, ink centimeter markings are added to the tube, a hydrophilic coating is deposited on the tube, and/or, pigtail coils are formed at the end or ends of the tube.

As indicated above, one technique for identifying appropriate drill sites for holes is the use of light transmission. Placing the de-molted tube between a light source or illuminator and a detector or sensor such as a camera, light transmission through the tube can be detected. As more light will be transmitted through the wire-free portions of the tube and less light through the wire-containing portions, the camera will detect a series of light-dark sections.

As will be appreciated, this detection system may be automated, such that the tubing is moved relative to the drill and the drill is automatically directed to incorporate holes only in light sections of the tube according to an algorithm programmed in a processor. Alternatively, the drill may be directed to incorporate holes anywhere except dark sections of the tube, or within a specified distance of a dark section. For example, if the pitch of the wire coil in the tube is approximately 4 mm, the drill can be directed to detect a dark band and drill approximately 1 to 2 mm on either side of the dark band. Of course, the drill may penetrate both sidewalls in one pass of the drill or enter by a shorter distance to penetrate only one sidewall in one pass.

Alternate methods of light transmission detection are also contemplated by the present invention. For example, instead of directing light through the tube from the exterior, light can be directed through the interior of the tube, for example by a light fiber, and the light/dark sections detected by a detector such as a camera, sensor, image processor or light meter. At least one information pertaining to the light and dark sections is transmitted to a processor and analyzed according to an algorithm to direct the drill safely through the light sections.

Various modifications to the manufacturing process can enhance light-dark contrast of the de-molted tube sections and allow for variable size holes. For example, the pitch of the wire coil can be increased to provide a larger target for drilling holes or to allow the drilling of larger diameter holes. As will be appreciated, the desired minimum size of the hole will depend on the surface tension of the fluid passing through the drainage hole and maximum size of the hole will depend on the inner diameter of the tube into which the hole is drilled. The size of the hole can be increased beyond the limits of the inner tube diameter by drilling an oval-shaped or elongate hole having a major axis that is substantially parallel to the axis of the tube.

In one embodiment of the present invention, in step one of the de-molting manufacturing method, a coated wire is alternatively wound with a filament comprising a polymer material around the mandrel to thereby increase the pitch of the wire coil. This will increase the width of the light sections when light is passed through the de-molted tube and provide more tolerance in selecting the drill site for holes. In one variation, the polymer of the wire coating and of the filament is the same. In another variation, the filament comprises a softer material than the coating on the wire. The wound coated wire would perform like a spring coil while the softer filament would behave as the more compliant body of the tube allowing kink-resistant bending and twisting. The difference in the durometer of the two materials does not need to be substantial.

Optionally, in order to further distinguish between the wire and non-wire sections, colorant may be added to either the polymer used to coat the wire or the plastic filament or both. Alternatively, different amounts of the same colorant or different colorants having different light transmission characteristics may be added to each of the polymer coating the wire and the plastic filament. Wire and non-wire sections may then be determined either by detecting light transmission through the tube or by direct visual inspection, with holes being added to those portions of the tube having the color characteristics of the plastic filament. Alternatively, a transparent polymer may be used either to coat the wire or in the plastic filament, or both.

Figure 3A:
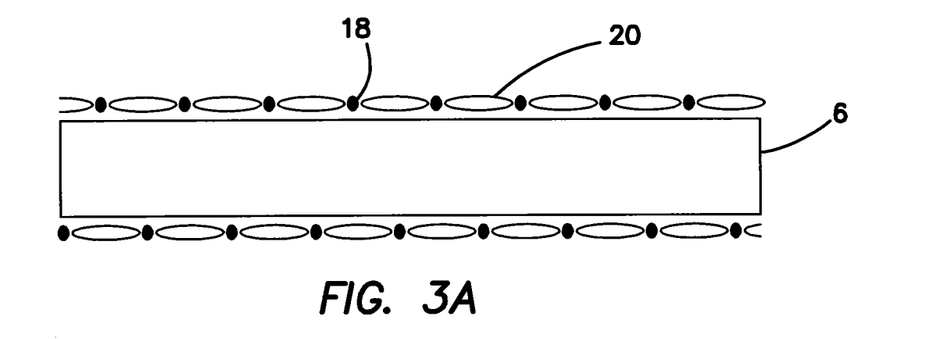
FIGS. 3A-3C show a method for manufacturing a thin walled, kink resistant tube having drainage holes, by alternatively winding an uncoated wire with a polymeric filament having an oval cross-section around a mandrel.
Figure 3B:
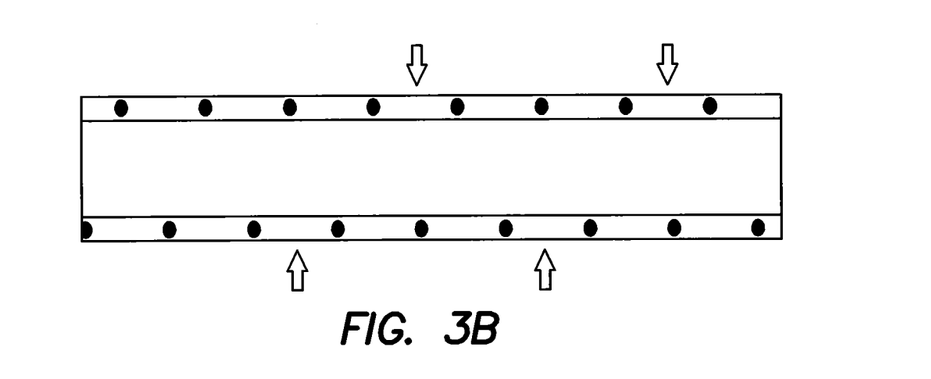
Figure 3C:
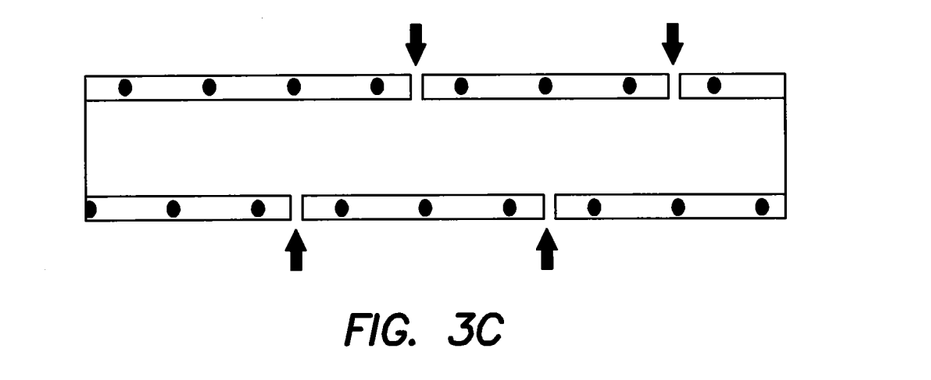

With particular reference to FIG. 3A, in one embodiment, the plastic filament has an oval cross-section, with the minor axis approximately equal to the diameter of the wire and the major axis larger than the diameter of the wire. The plastic filament is wound around the mandrel with its major axis generally parallel to the axis of the mandrel, allowing the pitch of the wire coil to be varied according to the major axis of the plastic filament while maintaining the same height as the coated wire. FIG. 3A shows a cross-section of a mandrel 6 wound alternatively with polymer-coated or non-coated wire 18 and a plastic filament 20 having an oval cross-section. FIG. 3B shows the same tube after de-molting, with the wire coils separated by larger target drilling sites, indicated by open arrows. FIG. 3C shows the tube with the drilled holes in locations indicated by solid arrows.

Figure 4:
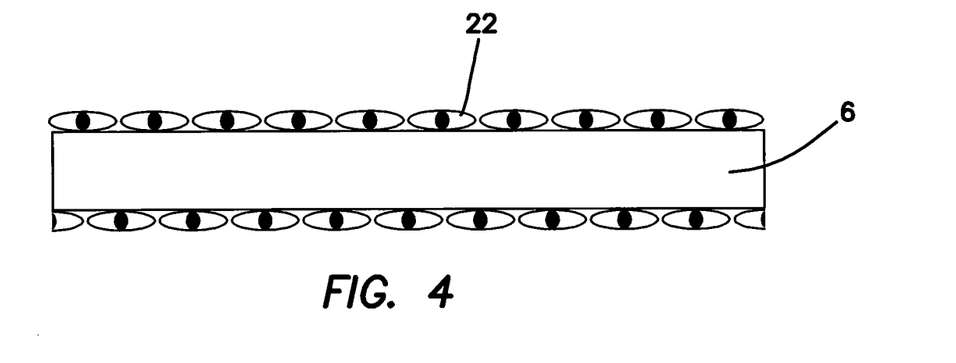
FIG. 4 shows a method for manufacturing a thin walled, kink resistant tube by winding a wire coated with polymer having an oval cross-section around a mandrel.

In an alternative embodiment shown in FIG. 4, in step one of the de-molting process, the wire is coated with a polymer having an oval profile. The coated wire 22 is wound around the mandrel with the major axis of the coated wire generally parallel to the axis of the mandrel as shown in FIG. 4. As the polymer melts during step two of the de-molting process, a polymer-filled space is produced between coils of the wire into which holes may be introduced without nicking or cutting the wire.

As described above, light transmission is a preferred method of detecting the non-wire portions of a tube for identifying hole drill sites. It is relatively inexpensive and efficient, and lends itself to automation. However, the present invention contemplates and encompasses other means of detection as well. For example, ultrasound or x-rays may used to distinguish between the wire-containing and non-wire sections. Alternatively, a hardness gauge may be used to identify the relatively harder wire sections. Also conductivity measurements may be made by passing an electrical current through the wire to distinguish the conductive wire sections from the non-conductive polymer sections.

Figure 5:
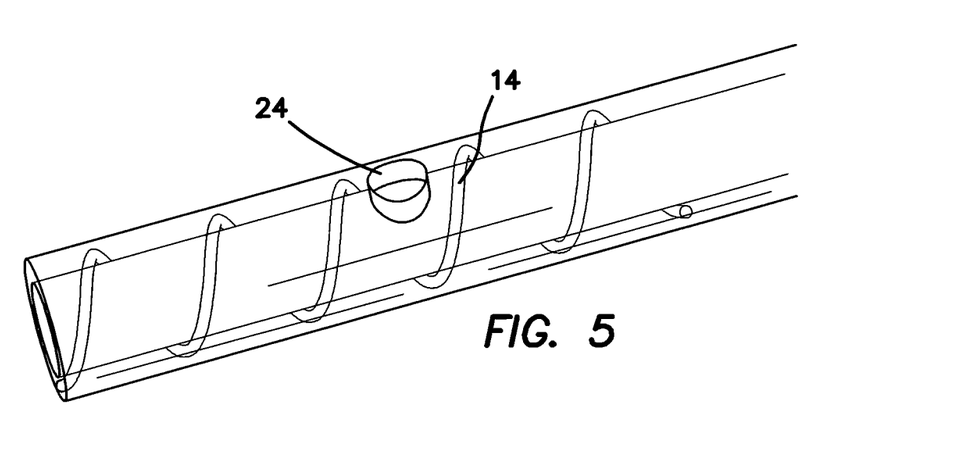
FIG. 5 is a perspective view of a wire-reinforced, thin walled, kink resistant tube with a drainage hole drilled between wire coils in the tube.

Holes may be introduced into the tubing by various processes, including but not limited to drilling, punching and melting. The holes may be formed in various shapes, including but not limited to a circle or an oval. See FIG. 5 for an example of a circular hole 24 introduced into the non-wire section of a tube according to the process of the present invention.

As referenced above, the present method may be automated to produce wire-reinforced tubing having drainage holes. It is important to note that this process may be used on tubing manufactured by a process other than the de-molting process, so long as the wire reinforcement and the hole target areas of the tube have different light transmission characteristics.

Figure 6A:
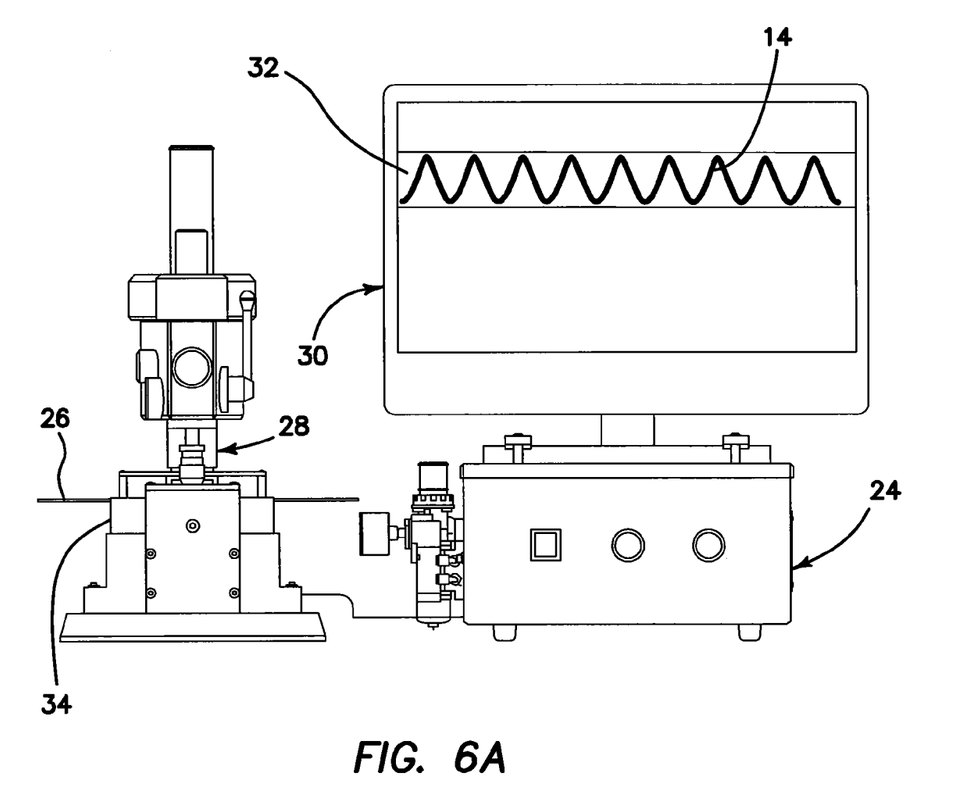
FIGS. 6A-6C are illustrations of (A) a front view of the drill, control box, and display monitor, (B) a hole drilling area, and (C) a close-up of the hole drilling area.
Figure 6B:
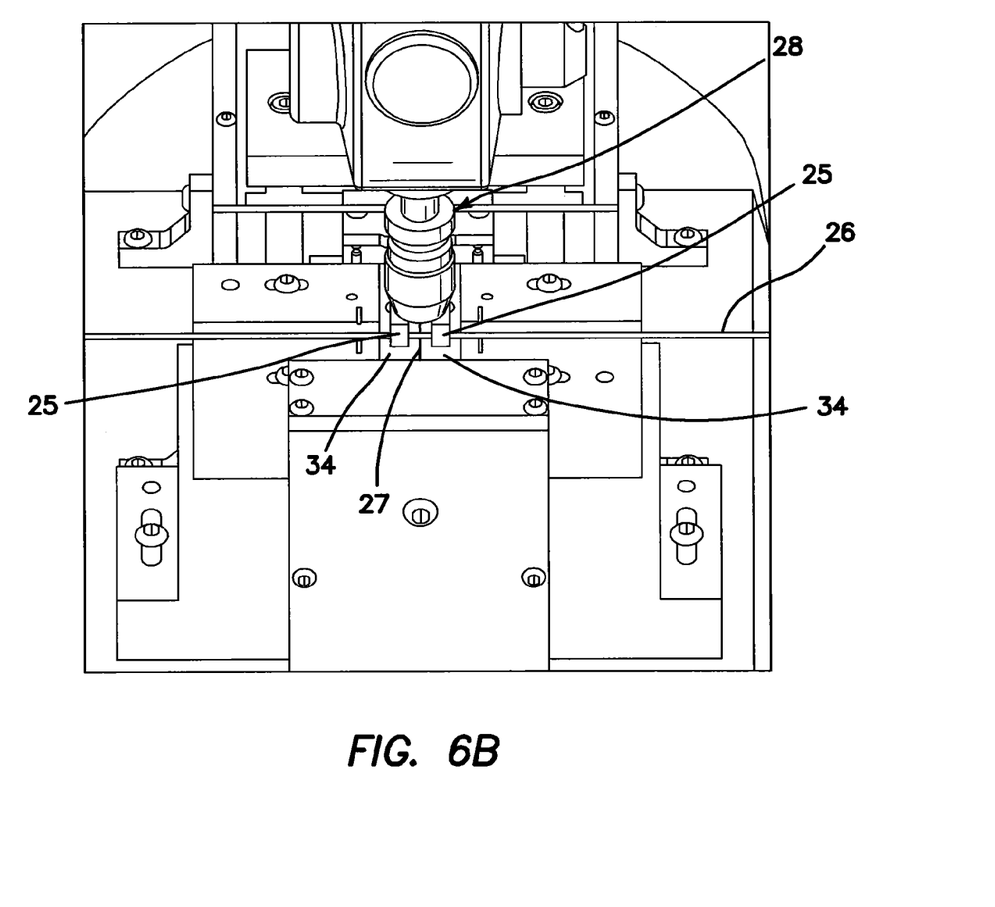
Figure 6C:
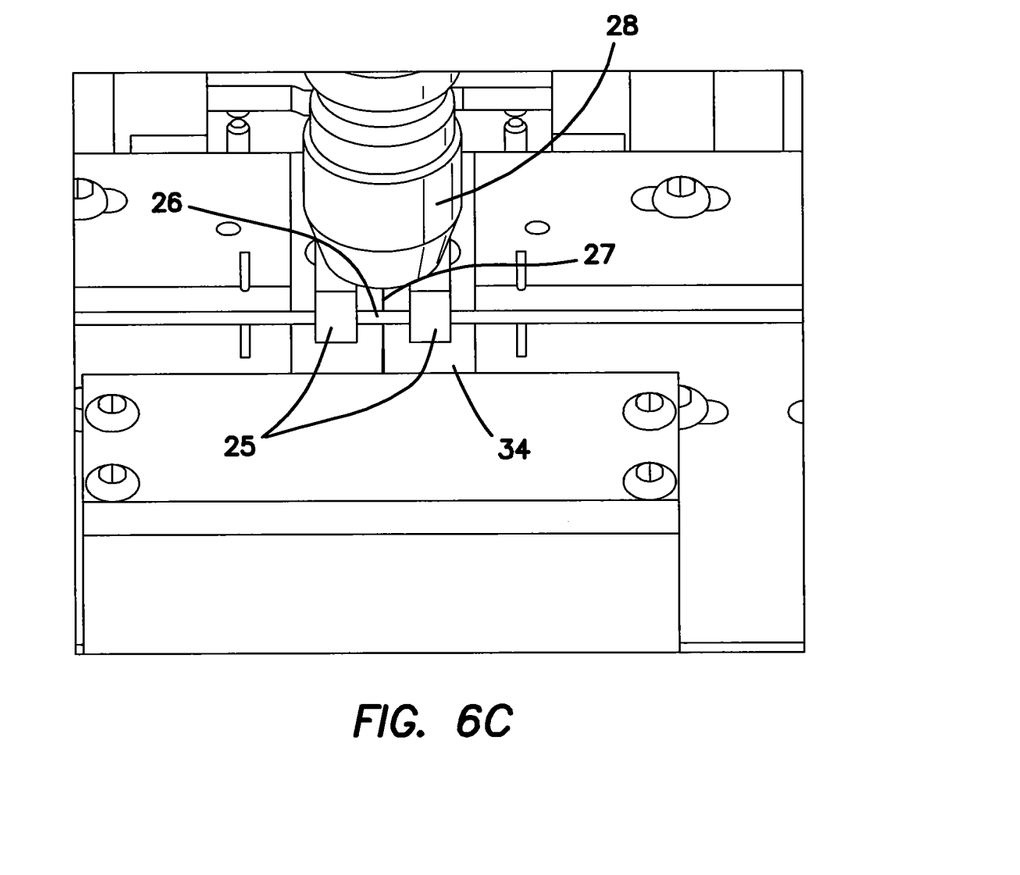

FIGS. 6A-6C show an example of a manufacturing set-up for the present method of introducing drill holes. The manufacturing set-up includes drill assembly 28 connected to a computer/microprocessor control box 24 and display monitor 30. As seen in FIGS. 6B and 6C, a wire-reinforced tube 26 secured with tubing immobilizers 25 is placed beneath a drill assembly 28 on a light source 34. The drill assembly 28 includes a coring needle 27 connected to a reciprocating motor and arranged to be substantially perpendicular to the surface of the tube 26. The drill assembly 28 further includes detection means including software and hardware configured to run on the microprocessor in the control box 24 including but not limited to an x-ray, image capture, light sensor, an optical system including an optical train of lenses and filters for image capture, intensity, color and/or image analysis, camera and electrical conductivity meter. Image capture is displayed on the display monitor 30 showing an image such as of an illuminated tube 32 as illustrated in FIG. 6A. Typical algorithms known to one having ordinary skill in the art are run by the microprocessor to analyze the image and identify target non-wire containing sections of the sheath. Target drill site analysis is conducted by the microprocessor and the drill needle is directed to penetrate the tube 26 at the appropriate locations. The tube 32 is moved above the light source to position the next drill target location of the tube 32 beneath the needle 27 to drill the subsequent hole.

The foregoing disclosure and description of the invention are illustrative and explanatory thereof, and various changes in the size, shape and materials, as well as in the details of the illustrated construction, may be made without departing from the spirit and scope of the invention. For these reasons, the above description should not be construed as limiting the invention, but should be interpreted as merely exemplary of preferred embodiments.

We claim:

1. A method for manufacturing a kink-resistant tube having holes, comprising:
   coating a wire with a plastic material;
   winding the coated wire into a single coil around a mandrel forming a plurality of windings;

heating the wound coated wire until the plastic material of the wire melts and bonds the windings forming a wire-reinforced sheath having wire-containing sections and polymer-filled non-wire containing sections;

removing the sheath from the mandrel;

placing the wire-reinforced sheath between a source of light and a camera after removing the sheath from the mandrel;

directing light through the sheath from the exterior source of light;

identifying at least one non-wire containing section;

detecting with the camera adjacent darker wire-containing sections relative to the lighter non-wire containing sections using light transmission through the coated wire;

drilling through the detected lighter sections; and forming at least one hole in the non-wire containing section.

2. The method of claim 1 further including the step of using light transmission through the wire-reinforced sheath to identify the non-wire containing sections.

3. The method of claim 2 wherein the step of identifying at least one non-wire containing section includes using a light sensor to detect relative light and dark areas.

4. The method of claim 3 wherein the step of coating the wire having a longitudinal axis includes coating a wire with plastic material formed into an elongate cross-section taken perpendicular to the longitudinal axis.

5. The method of claim 4 wherein the step of winding the wire around the mandrel such that the major axis of the elongate cross-section is substantially parallel to the longitudinal axis of the mandrel.

6. The method of claim 1 wherein the step of forming at least one hole includes forming an elongate hole having a major axis substantially parallel to the longitudinal axis of the sheath.

7. The method of claim 1 wherein the step of identifying at least one non-wire containing section includes the step of detecting at least one wire-containing section.

8. A method for manufacturing a kink-resistant tube having holes, comprising:

coating a wire with a plastic material;

winding the coated wire into a single coil around a mandrel forming a plurality of windings;

heating the wound coated wire until the plastic material of the wire melts and bonds the windings forming a wire-reinforced sheath having wire-containing sections and polymer-filled non-wire containing sections;

removing the sheath from the mandrel;

placing the wire-reinforced sheath between a source of light and a camera after removing the sheath from the mandrel;

directing light through the sheath from the exterior source of light;

identifying at least two adjacent wire containing sections;

detecting with the camera adjacent darker wire-containing sections relative to the lighter non-wire containing sections using light transmission through the coated wire;

drilling through the detected lighter sections; and forming at least one hole between the two adjacent wire-containing sections.

9. The method of claim 8 further including passing a light through at least one wall of the wire-reinforced sheath.

10. The method of claim 8 further including the step of increasing the pitch of the wire coil to increase the width of the light sections when light is passed.

11. The method of claim 1 further including the step of directing a drill to incorporate holes anywhere except dark sections of the sheath.

12. The method of claim 1 further including the step of directing a drill to incorporate holes within a specified distance of a dark section.

13. The method of claim 1 further including the step of transmitting at least one information pertaining to the light and dark sections to a processor.

14. The method of claim 13 further including the step of analyzing the at least one information according to an algorithm to direct a drill safely through the light sections.

* * * * *